US 8,949,041 B2

(12) United States Patent
Schenk et al.

(10) Patent No.: US 8,949,041 B2
(45) Date of Patent: Feb. 3, 2015

(54) SYSTEM AND METHOD FOR MONITORING HEALTH OF A FLUID SEAL MEMBER

(75) Inventors: Douglas Schenk, Chula Vista, CA (US); Jeffrey D. Navarro, Chula Vista, CA (US)

(73) Assignee: Parker-Hannifin Corporation, Cleveland, OH (US)

( * ) Notice: Subject to any disclaimer, the term of this patent is extended or adjusted under 35 U.S.C. 154(b) by 580 days.

(21) Appl. No.: 13/295,155

(22) Filed: Nov. 14, 2011

(65) Prior Publication Data

US 2012/0143519 A1 Jun. 7, 2012

Related U.S. Application Data

(60) Provisional application No. 61/418,987, filed on Dec. 2, 2010.

(51) Int. Cl.
*G01N 33/44* (2006.01)
*G01M 3/02* (2006.01)
(Continued)

(52) U.S. Cl.
CPC ............... *F16J 15/064* (2013.01); *G01M 3/02* (2013.01); *G01N 33/445* (2013.01); *G06F 19/00* (2013.01); *G06F 17/40* (2013.01)
USPC ............. 702/34; 73/12.01; 73/49.8; 277/321; 702/1; 702/42

(58) Field of Classification Search
CPC ............. F16J 15/00; F16J 15/02; F16J 15/06; F16J 15/064; G01D 7/00; G01D 9/00; G01D 21/00; G01L 1/00; G01L 5/00; G01L 25/00; G01M 3/00; G01M 3/02; G01M 3/04; G01M 3/16; G01M 3/18; G01M 3/183; G01M 99/00; G01M 99/007; G01N 3/00; G01N 3/56; G01N 17/00; G01N 33/00; G01N 33/44; G01N 33/445; G01N 2033/00; G01N 2203/02; G01N 2203/06; G01N 2203/0617; G01N 2203/067; G01N 2203/0676; G06F 11/00; G06F 11/30; G06F 11/32; G06F 11/34; G06F 15/00; G06F 15/16; G06F 17/00; G06F 17/10; G06F 17/40; G06F 19/00
USPC ......... 73/1.01, 12.01, 12.08, 37, 40, 46, 49.8, 73/432.1, 760, 865.8, 865.9, 866.3; 137/551; 277/317, 318, 319, 320, 321; 285/93, 95; 702/1, 33, 34, 41, 42, 43, 702/127, 138, 182, 187, 189; 708/100, 105, 708/200
See application file for complete search history.

(56) References Cited

U.S. PATENT DOCUMENTS 3,115,772 A * 12/1963 O'Keeffe et al. ............... 73/820
3,161,040 A * 12/1964 Ver Halen .......................... 73/46
(Continued)

*Primary Examiner* — Edward Cosimano
(74) *Attorney, Agent, or Firm* — Renner, Otto, Boisselle & Sklar, LLP

(57) ABSTRACT

A system and for determining health of a fluid seal member including a fluid seal member; a transducer in force transmitting contact with the fluid seal member to generate an output signal based on an amount of force and/or pressure applied to the transducer; a radio frequency (RF) transponder operably coupled to the transducer to store the output signal of the transducer; a reader within an operable distance from the RF transponder to transmit electromagnetic energy to the RF transponder and receive the output signal of the transducer stored in the RF transponder through a radio frequency communication link; and a processor coupled to the reader, to determine health of the fluid seal member.

22 Claims, 11 Drawing Sheets

(51) Int. Cl.
*G06F 17/40* (2006.01)
*G06F 19/00* (2011.01)
*F16J 15/06* (2006.01)

(56) References Cited

U.S. PATENT DOCUMENTS

| | | | |
|---|---|---|---|
| 3,180,135 A * | 4/1965 | Cain, Jr. et al. | 73/46 |
| 3,362,217 A * | 1/1968 | Rush et al. | 73/112.01 |
| 5,540,448 A * | 7/1996 | Heinzen | 277/321 |
| 5,785,323 A * | 7/1998 | Heinzen | 277/582 |
| 6,012,020 A | 1/2000 | Gardell et al. | |
| 6,595,523 B1 * | 7/2003 | Heinzen | 277/321 |
| 6,615,639 B1 * | 9/2003 | Heinzen | 73/7 |
| 6,734,791 B2 | 5/2004 | Kelly et al. | |
| 6,978,669 B2 | 12/2005 | Lionetti et al. | |
| 7,070,053 B1 | 7/2006 | Abrams et al. | |
| 7,158,034 B2 | 1/2007 | Corbett, Jr. | |
| 7,274,289 B2 | 9/2007 | Kerr et al. | |
| 7,405,818 B2 * | 7/2008 | Heinzen | 356/246 |
| 2004/0075218 A1 * | 4/2004 | Heinzen | 277/321 |
| 2007/0186644 A1 | 8/2007 | Lazar et al. | |
| 2009/0107233 A1 | 4/2009 | Kassem | |

* cited by examiner

SYSTEM AND METHOD FOR MONITORING HEALTH OF A FLUID SEAL MEMBER

RELATED APPLICATIONS

This application claims the benefit of U.S. Provisional Application No. 61/418,987 filed Dec. 2, 2010, which is hereby incorporated herein by reference.

FIELD OF THE INVENTION

The invention herein described relates to a system and method for monitoring health of fluid seal members in order to facilitate a proactive approach to preventive maintenance.

BACKGROUND

Generally it is difficult to predict the useful life of a fluid seal member. Conventional methods utilize finite element analysis (FEA) and lab testing to predict the health or expected lifetime of a fluid seal member. However, such conventional methodologies have drawbacks. For example, FEA is predictive and many assumptions are made when using FEA to predict how a fluid seal member will respond in its environment. Material testing performed on fluid seal members may also be used to predict how such fluid seal members will react in certain sealing environments. These environments are estimated at the time of design and this testing is limited to the precise conditions of the lab environment. Some fluid seal members may go through validation testing. Validation testing generally involves testing the fluid seal member in a specific environment. Such validation testing is limited to the specific environment tested and is expensive.

SUMMARY OF THE INVENTION

The present invention addresses the above problems by providing a system and method that provides a proactive approach to preventive maintenance by monitoring a physical parameter associated with the seal and correlate the monitored data to a predictive failure.

One aspect of the invention relates to 1. A system for determining health of a fluid seal member, the system including: a fluid seal member; a transducer in force transmitting contact with the fluid seal member, wherein the transducer is operable generate an output signal based on an amount of force and/or pressure applied to the transducer; a radio frequency (RF) transponder operably coupled to the transducer, wherein the RF transponder is configured to store the output signal of the transducer; a reader within an operable distance from the RF transponder, wherein the reader is selectively controlled to transmit electromagnetic energy to the RF transponder and receive the output signal of the transducer stored in the RF transponder through a radio frequency communication link; and a processor coupled to the reader, wherein the processor is operable to determine health of the fluid seal member based on the received output signal of the transducer, wherein the processor correlates the received output signal to a compression set and determines health of the fluid seal member by the amount of compression set imparted in the fluid seal member.

Another aspect of the invention relates to A method for determining health of a fluid seal member, the method including: measuring force and/or pressure transmitted to the fluid seal member by a transducer in force transmitting contact with the fluid seal member and outputting an output signal corresponding to the measured force and/or pressure; storing a representation of the output signal in a radio frequency (RF) transponder coupled to the transducer; reading the representation of the output signal stored in the RF transponder by a reader, wherein the reader is selectively controlled to transmit electromagnetic energy to the RFID transponder and receive the output signal of the transducer through a radio frequency communication link; and processing the received output signal by a processor, wherein the processing includes determining health of the fluid seal member based on the received output signal of the transducer by correlating the received output signal to a compression set and determine health of the fluid seal member by the amount of compression set imparted in the fluid seal member.

Further features of the invention will become apparent from the following detailed description when considered in conjunction with the drawings. In addition, while a particular feature of the invention may have been described above with respect to only one or more of several illustrated embodiments, such feature may be combined with one or more other features of the other embodiments, as may be desired and advantageous for any given or particular application.

BRIEF DESCRIPTION OF THE DRAWINGS

In the annexed drawings.

DETAILED DESCRIPTION

Figure 1:
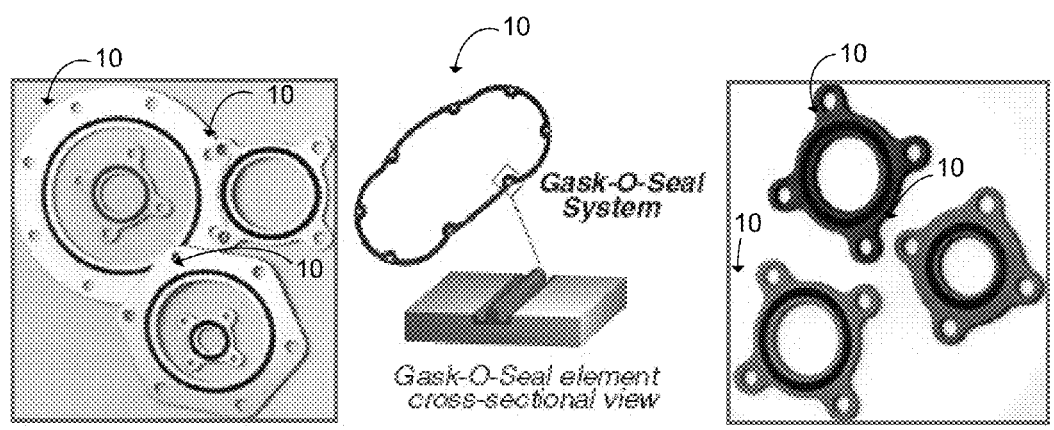
FIG. 1 are views of fluid seal members in accordance with aspects of the invention.

Referring now in detail to the drawings and initially to FIG. 1, an exemplary fluid seal member 10 is illustrated in a variety of embodiments. The fluid seal member 10 may be made from any material that is suitable to prevent the transfer of liquid through the material. Typically, the fluid seal member 10 is made from an elastomeric material. Suitable elastomeric materials include, for example, a natural rubber, a synthetic rubber, etc. An exemplary seal in accordance with aspects of the present disclosure is a Gask-O-Seal, manufactured by the assignee of the present invention, Parker-Hannifin Corporation. A Gask-O-Seal may be metal, plastic, or composite retainers with a machined groove in the retainer plate into which a custom engineered rubber element is molded. The elastomer seal may be mechanically and/or chemically bonded to create a dependable, responsive seal for flat or curved surfaces, as illustrated in FIG. 1.

The Gask-O-Seal offers a variety advantages over other seals including, for example: quick and easy installation—a one-piece solution; no re-torquing required due to metal-to-metal contact; leak-proof sealing capability; extended service life; and reusability.

Figure 2:
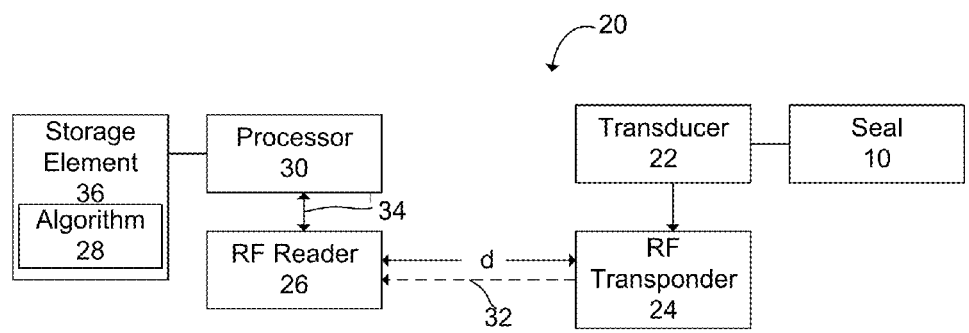
FIG. 2 is an exemplary system in accordance with aspects of the invention.

Referring to FIG. 2, an exemplary system 20 for determining health of the fluid seal member 10 is illustrated. The system includes: a fluid seal member 10, a transducer 22, a radio frequency (RF) transponder 24, a reader 26 and a computer algorithm 28 executed by an associated processor 30, for example. In operation, the transducer 22 is in force transmitting contact with the fluid seal member 10. The transducer 22 is operable generate an output signal based on an amount of force and/or pressure applied to the transducer 22. The RF transponder 24 is operably coupled to the transducer 22 to store the measured force and/or pressure value received from the transducer 22. The RF transponder 24 may from time to time output the measured force and/or pressure value to the reader 26. The reader 26 is within an operable distance "d" from the RF transponder 24. The operable distance "d" may vary based on the type of RF communication used to communicate between the reader 26 and the RF transponder. For example, if the RF transponder is a radio frequency identification (RFID) transponder an operable distance may be up to 10 centimeters, for example. The operable distance "d" may be closer and/or farther if another RF communication medium is used.

The RF reader 26 is selectively controlled by the processor 30 to transmit electromagnetic energy to the RF transponder 24. In return, the reader 26 receives the output signal of the transducer 24 through an RF communication link 32. The received output signal may be then be processed by computer algorithm 28, which may be executed by the associated processor 30, to determine health of the fluid seal member 10 based on the received output signal of the transducer 22, as explained in further detail below.

The transducer 22 may be any suitable force and/or pressure sensing device that is configured to measure a force and/or pressure applied to the fluid seal member 10. For example, the transducer 22 may be a force transducer and/or a pressure transducer or any other suitable sensor (e.g., a strain sensor or other sensor configured to detect a physical property under which the fluid seal member is experiencing.

The transducer 22 may be in direct contact with the fluid seal member and/or may have one or more intervening structures configured to measure the force applied to the fluid seal member 10. Preferably such structures are inelastic in order to more closely correlate the force and/or pressure applied to the fluid seal number 10 through the transducer 22.

In one embodiment, the RF transponder 24 is coupled to the transducer 22 by a wire or other suitable mechanical mechanism. The RF transponder 24 may be may an RFID transponder. As such, the RF transponder 24 may be an active tag or a passive tag. The RFID transponder is configured to store and/or output an output signal that is indicative of the force and/or pressure that the transducer 22 is subjected to. In one embodiment, the output signal is a bit value.

RFID is a technology that uses radio waves to transfer data from an electronic tag, called RFID tag or label, through a reader for the purpose of reading the tag, for example. The RFID tag's information is stored electronically. The RFID tag includes a radio frequency (RF) transmitter and receiver. Generally, RFID tags utilize near field communications (NFC) to communicate in one of two communication modes (e.g., passive or active communication modes).

In the passive mode, a RFID reader (e.g., RF reader 26) transmits an encoded radio signal to interrogate the tag. The tag receives the message and responds with information stored on the tag. For example, in the passive mode, the reader may modulate the carrier waves corresponding to the electromagnetic waves that it generates, so as to send data to the RF transponder 24. The RF transponder 24 generally modulates the carrier waves corresponding to the electromagnetic waves generated by the RFID reader and sends the resulting information, in the form of a bit value, NFC tag or other information format to the RFID reader 26.

In the active mode, RFID reader 26 and RF transponder 24 both modulate the carrier waves corresponding to the electromagnetic waves generated by themselves so as to send information (e.g., bit data, NFC tags, etc.). When the near field communication based on electromagnetic induction is performed, the apparatus that outputs electromagnetic waves first to initiate the communication and may be said to take the initiative is called an initiator. The initiator transmits a command to a communicating party, and the communicating party sends a response associated with the command so as to establish the near field communication. The communicating party who sends the response to the command received from the initiator is called a target. For example, if RF reader 26 begins outputting electromagnetic waves to start communication with the RF transponder 24, then the RF reader 26 will be the initiator and the RF transponder 24 will be the target.

In the passive mode, RF reader 26, which is the initiator, continues outputting electromagnetic waves. Alternatively, the reader 26 may periodically poll the RF transponder 24. The reader 26 modulates the electromagnetic waves generated by itself so as to send data to the RF transponder 24, which is the target. The RF transponder 24 carries out load-modulation on the electromagnetic waves output from the reader 26, which is the initiator, and sends information to the reader 26.

In the active mode, when the RF reader 26, which is the initiator, sends information, it generally first starts outputting electromagnetic waves by itself, and modulates the generated electromagnetic waves so as to send data to the target, i.e., the RF transponder 24. The RF reader 26 may stop outputting electromagnetic waves after the completion of the transmission of data. When the RF transponder 24, which is the target, sends data, it begins outputting electromagnetic waves by itself, and modulates the electromagnetic waves so as to send data to the RF reader 26, which is the initiator. The RF transponder 24 may stop the output of the electromagnetic waves after the transmission of data is finished.

One of ordinary skill in the art will readily appreciate that the above discussion is exemplary in nature and in no way is intended to limit the scope of the present invention. Likewise, one of ordinary skill in the art will readily appreciate that the data exchanged between the RF reader and the RF transponder may contain a variety of information. Such information may include, for example, a number, a measured value, identification, temperature, a serial number, a model number, status information, etc.

The processor 30 is coupled to the RF reader 26. The processor 30 may be coupled to the RF reader 26 through any suitable mechanism. For example, the processor 30 may be coupled to the reader 26 through a communication link 34. The communication link 34 may be a wired communication link or a wireless communication link.

The processor 30, through the algorithm 28, is configured to cause the RF reader 26 to periodically and/or continuously poll the RF transponder 24 to read data stored in the RF transponder 24. The processor, through the algorithm 28, is also configured to convert the bit value received from the RF transponder 24 into a corresponding force and/or pressure value. The algorithm 28 may be stored in a storage element 36. The storage element 36 may be a memory, a hard disk drive, or any suitable storage device. In one embodiment, the storage element 36 is coupled to the processor 30. The storage element is operable to store bit values and/or pressure values for a plurality of time points.

The processor 30, through the algorithm 28, is configured to compare the bit values and/or the force and/or pressure values for a prescribed number of time points with reference data stored in the storage element to determine the health of the fluid seal member. As a person of ordinary skill in the art will readily appreciate, the storage element 36 may store the reference data as part of the algorithm 28 and/or separately from algorithm 28.

The reference data may include any information deemed desirable to determine the health of the fluid seal member 10. Such information includes but is not limited to, compression set information, pressure per square inch (PSI) drop, temperature information, time, experimental fluid seal load information, etc. In addition the reference data may include theoretical information. Such as theoretical compression set data, temperature correction coefficients, a temperature correction factor equation, etc. For example, the reference data may include one or more equations to convert force and/or pressure measured from the transducer 22 to a compression set value associated with the fluid seal member under test.

Figure 3A:
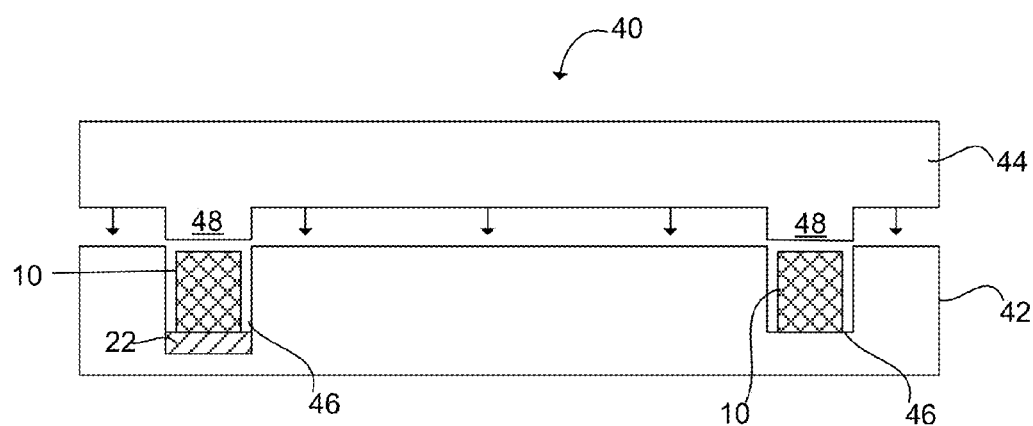
FIGS. 3A-3B are schematic views of an exemplary retainer in accordance with aspects of the invention.

Referring to FIG. 3A, a cross-section view of a retainer 40 for use with a fluid seal member 10 is illustrated. The retainer 40 is formed of a generally rigid metal, plastic, or composite material. The retainer 40 includes a first portion 42 and a second portion 44. The first portion 42 includes a groove 46 formed therein. The groove 46 may include sidewalls and a bottom wall. The groove 46 is configured to receive the fluid seal member 10. The second portion 44 may include a protrusion 48 that extends from the second portion 44. The protrusion 48 is configured to engage the fluid seal member 10 within the groove 46. The transducer 22 may be configured to be received by the groove 46 and/or be secured to the second portion, for example, on the protrusion 48.

Figure 3B:
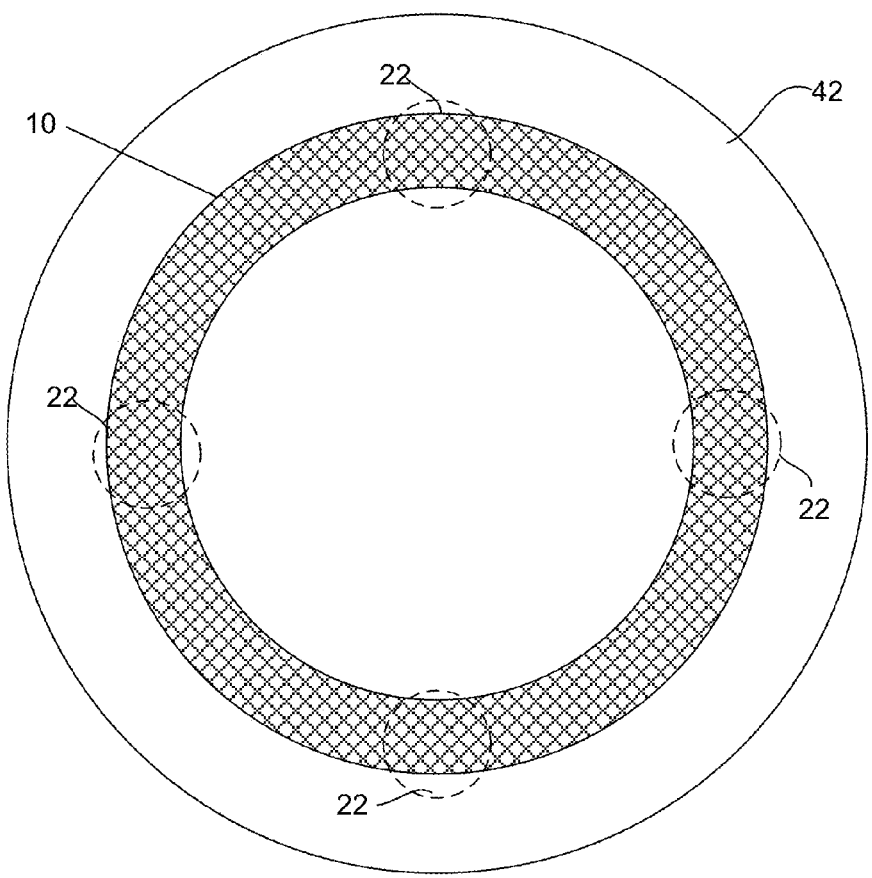

In one embodiment illustrated in FIG. 3B, there may be a plurality of transducers 22 spaced apart along the groove 46. As illustrated in FIG. 3B, the transducers 22 may be spaced apart in an equidistant manner. In another embodiment the transducers 22 may be spaced apart in any desired manner (e.g., non-symmetrical). The transducer 22 is mounted such that the transducer 22 is in force transmitting contact with the fluid seal element 10. In use, the first portion 42 and the second portion 44 are configured to secure the fluid seal number 10 in a compressed state. The transducer 22 is operable to detect at least one of a force and/or a pressure applied to one or more of the transducers 22.

As stated above, the RFID transponder 24 is coupled to the one or more transducers 22 and is operable to store signals received from the one or more transducers 22 and an output such signals and/or data values to the RF reader 26 when polled and/or otherwise communication is requested by RF reader 26.

Figure 4A:
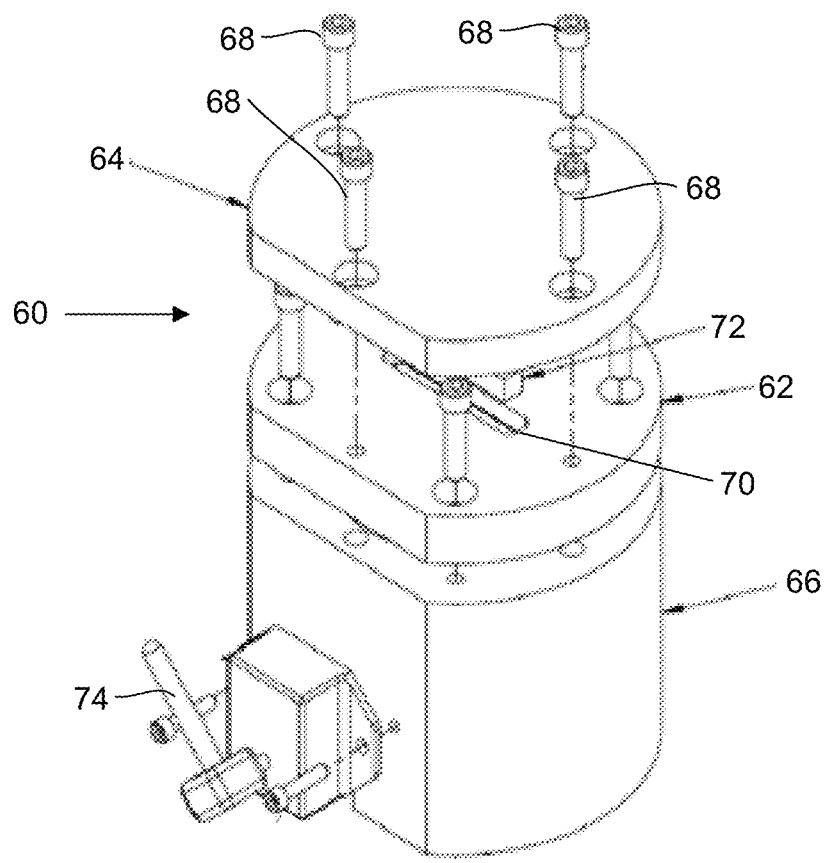
FIGS. 4A-4B are schematic views of exemplary fixture in accordance with aspects of the invention.

Referring to FIG. 4A, an exemplary fixture 60 in accordance with aspects of the present invention is illustrated. The fixture 60 includes a first portion 62, a second portion 64 and a base portion 66. The first portion 62 and the second portion 64 are releasably secured to the base portion 66 through one or more fastening mechanisms 68. An exemplary fastening mechanism 68 is a screw, a nail, a clamp, etc. The first portion 62 includes a groove 70 for receiving a fluid seal member 72. When the first portion 62 and the second portion 64 are secured to the base 66, a compressive force is applied to the fluid seal member 72, as discussed above.

Figure 4B:
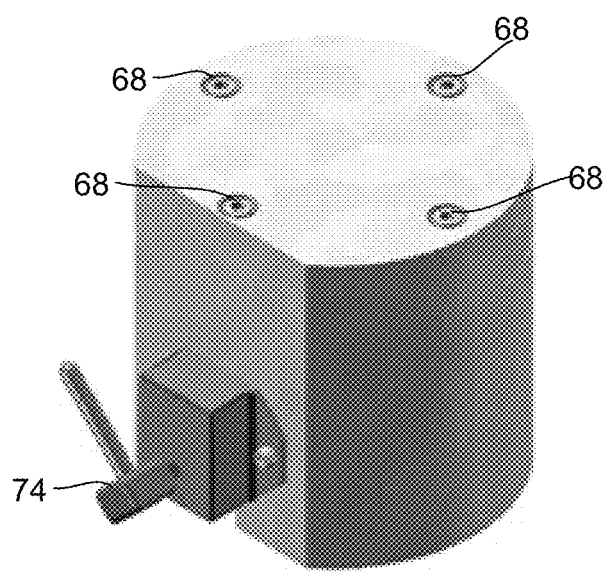

Referring to FIG. 4B, the exemplary fixture 60 is illustrated with fastening mechanisms 66 secured through the first portion 62, the second portion 64 and into the base 66. In such case, a compressive load is applied to the fluid seal member 72 and the transducer (not shown). The transducer is coupled to the RF transponder 74 for outputting signals generated by the one or more transducers to the reader and processor as discussed above.

Figure 5:
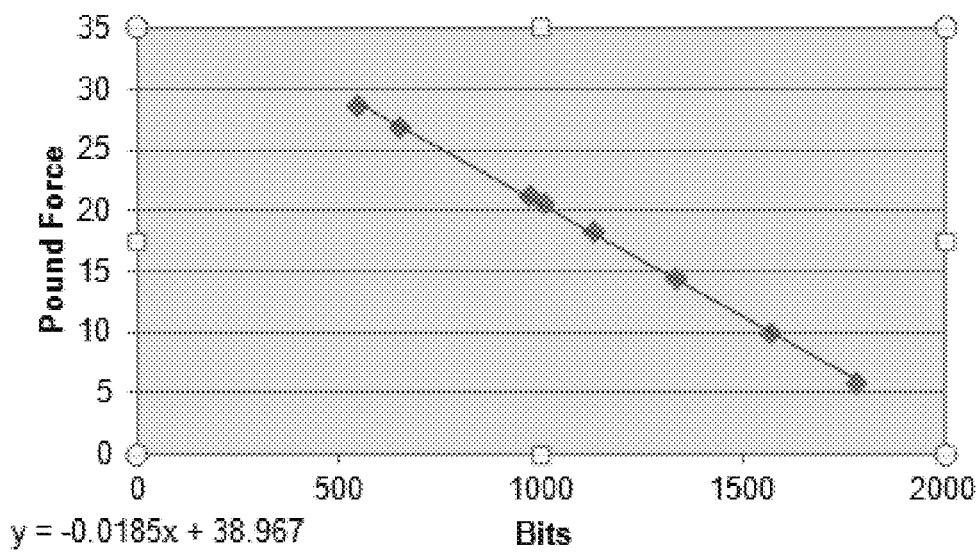
FIGS. 5-6 are exemplary charts illustrating linear characteristics of force and pressure as a function of bits in accordance with aspects of the invention.

FIG. 5 illustrates an exemplary load curve in accordance with aspects of the present invention. As illustrated, a linear relationship exists between force in pounds on the y-axis and the number of bits output on the x-axis. The linear relationship is characterized by the equation $y=-0.0185x+39.87$.

Figure 6:
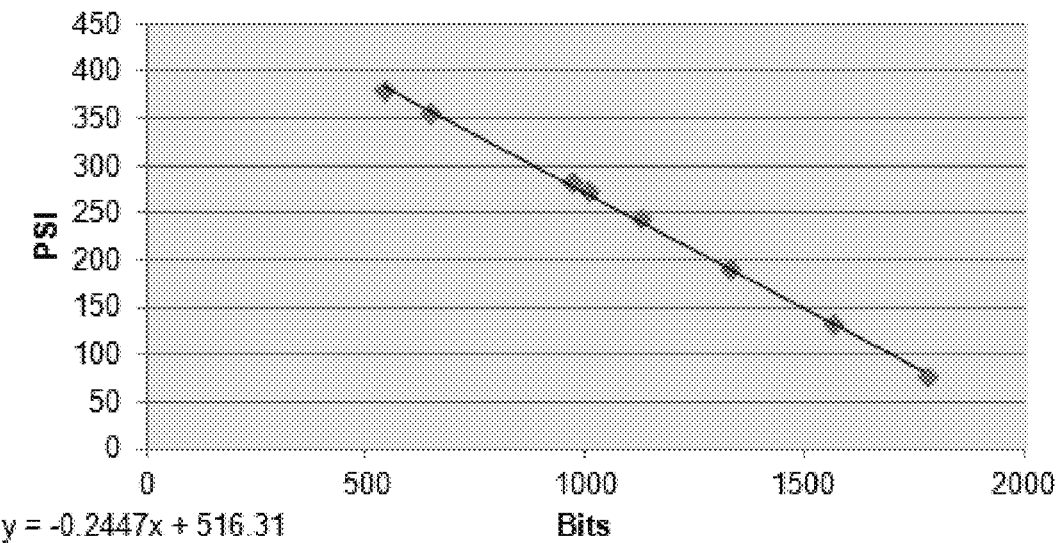

FIG. 6 illustrates a similar relationship between pounds per square inch (PSI) along the y-axis and the number of bits output on the x-axis. The linear relationship is characterized by the equation $Y=-0.2447x+516.31$.

Figure 7:
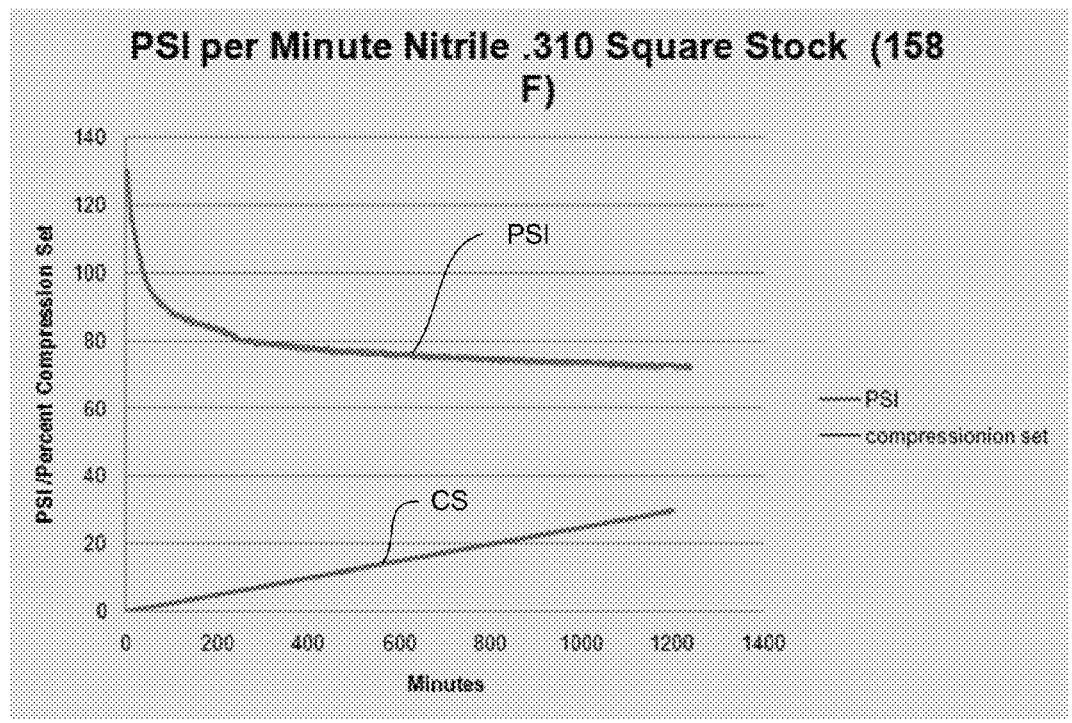
FIGS. 7-10 are exemplary charts illustrating test results of a fluid seal member at different temperatures in accordance with aspects of the invention.

FIG. 7 illustrates two exemplary load curves in accordance with aspects of the present invention. The top curve, labeled PSI, illustrates load dissipation measured by one or more of the transducers from the exemplary fixture 60. As can be seen from the graph, the curve illustrates an exponential decay over an initial period, for example, about 300 minutes. After the initial period, the force dissipates in a linear manner.

The lower curve of FIG. 7 illustrates compression set versus time. Compression set is the amount of deformation (expressed as a percentage of original dimensions) that a material retains after compressive stress is released.

For purposes of this invention, compression set refers to deformation to the fluid seal number. As can be seen from FIG. 7, compression set increases in a generally linear manner over time. In FIG. 7, the tests were performed at a temperature of 158° F. The fluid seal member was a 0.310 block of nitrile. Such testing was performed for proof of concept testing.

Figure 8:
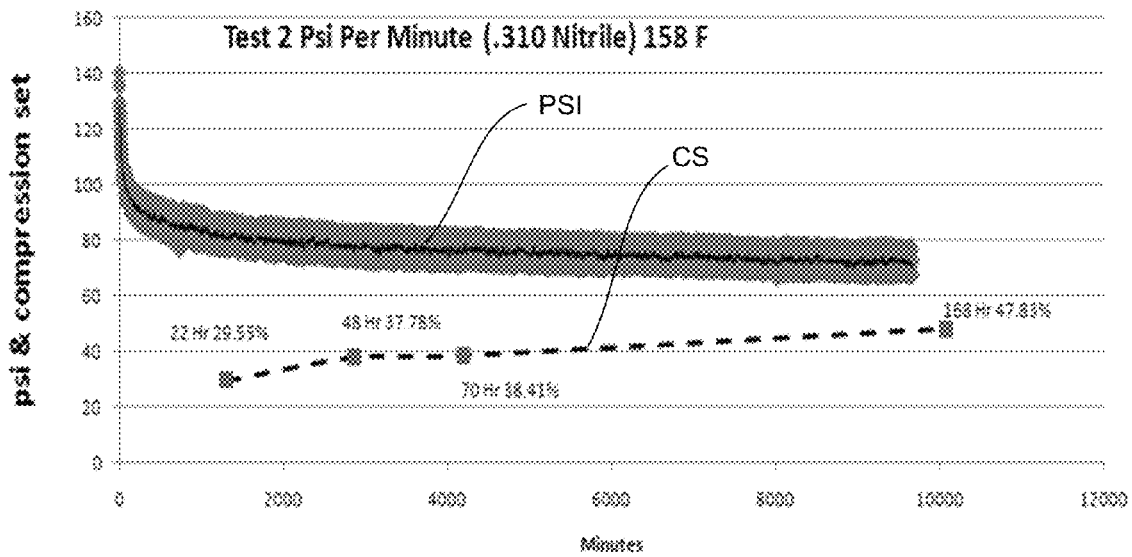

FIG. 8 illustrates a PSI load curve (upper curve) and a compression set load curve (lower curve) over an extended period time than illustrated in FIG. 7. FIG. 8 illustrates that over the extended period of time, the load curves are essentially linear.

Figure 9:
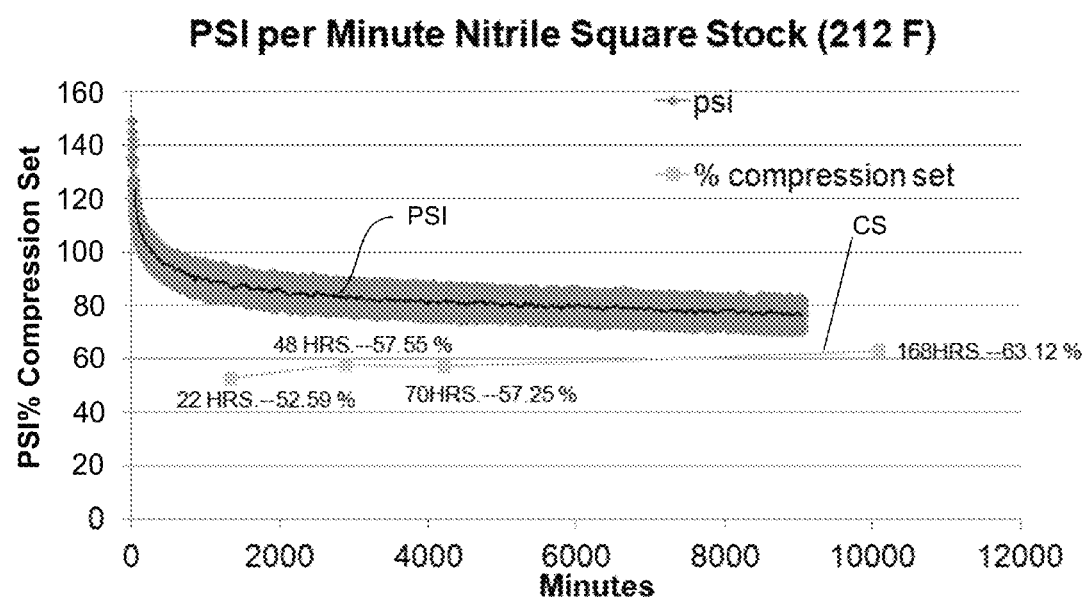

FIG. 9 illustrates two exemplary load curves in accordance with aspects of the present invention, similar to FIGS. 7 and 8 above. The PSI load curve (upper curve) illustrates the exponential dissipation in PSI in an initial region and a linear dissipation over an extended period of time. The compression set load curve (lower curve) illustrates a generally linear increase in compression set over an extended period of time. The following data points were collected in forming the compression set load curve: 52.59% at 22 hours; 57.55% at 48 hours; 57.25% at 70 hours; and 63.12% and 168 hours. For FIG. 9, the tests were performed at 212° F.

Figure 10:
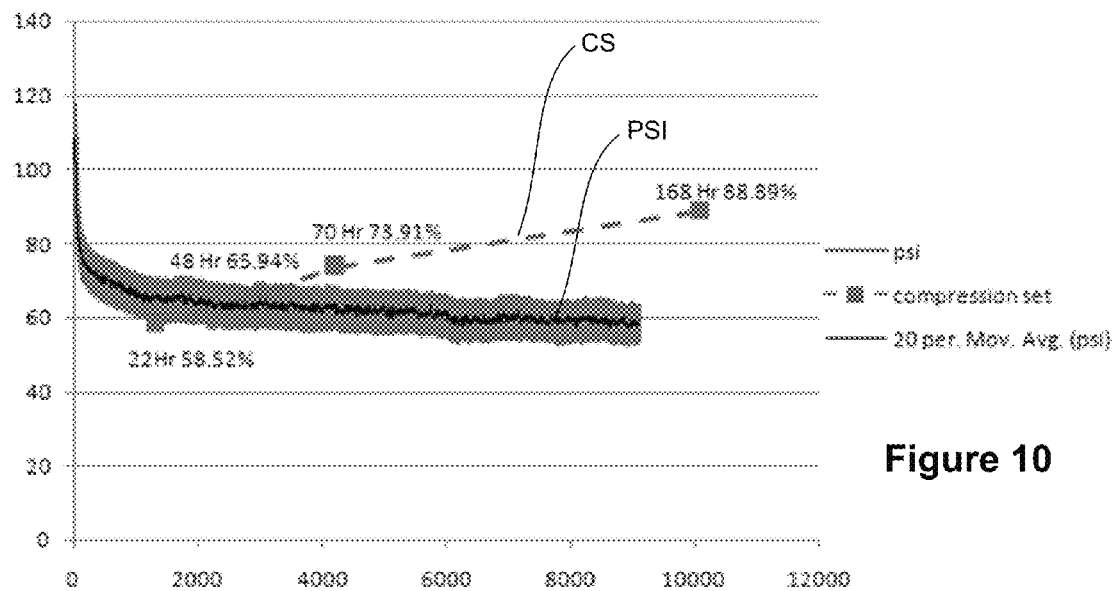

FIG. 10 illustrates load curves in accordance with aspects of the present invention. The PSI load curve (upper curve) illustrates the exponential dissipation in PSI in an initial region and a linear dissipation over an extended period of time. The compression set load curve (lower curve) illustrates a generally linear increase in compression set over an extended period of time. The following data points were collected in forming the compression set load curve: 58.52% at 22 hours; 65.94% at 48 hours; 73.91% and 70 hours; and 88.89% at 168 hours. For FIG. 10, the tests were performed at 257° F.

Figure 11:
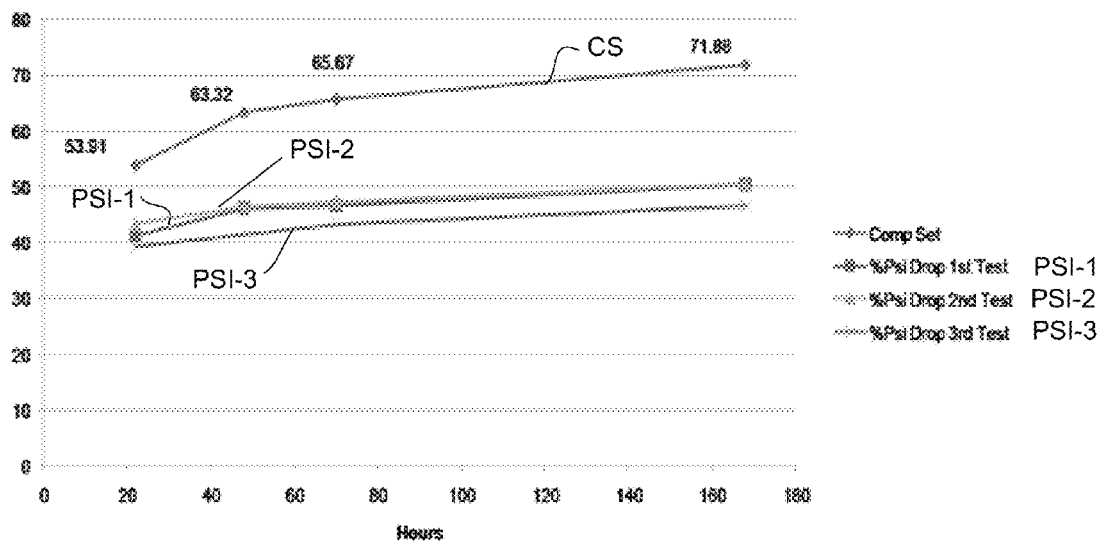
FIGS. 11, 12, and 13A-13C illustrate at least one of compression set, pressure, and theoretically calculated compression set as a function of time.

FIG. 11 is a graphical illustration of compression set (%) and pressure drop (%) as a function of time at a temperature of 257° F. The top graph labeled CS illustrates compression set as a function of time. For example, at time equals approximately 20 hours compression set is approximately 53.91%; at approximately 50 hours compression set is approximately 63.32%; at approximately 70 hours compression set is 65.67%; and that approximately 170 hours compression set at 71.88%.

The bottom three curves, PSI-1, PSI-2 and PSI-3, illustrates pressure drop in percent PSI for three separate tests. As can be seen from the graphs, data associated with PSI-1 and PSI-2 are substantially similar and have overlap. While the data associated with PSI-3 shows lower pressure drop than that associated with the PSI-1 and PSI-2 at the various points along the curve, the linear relationship for each of the test data is apparent.

A linear relationship between pressure drop and compression set for this test data yields a Temperature Correction Factor ($T_{CF}$) that is represented by the following equation:

$$T_{CF} = \frac{\overline{CS}}{\overline{\%\Delta P}}$$

where CS is average compression set; and a∆P is change in pressure expressed as a percentage.

Figure 12:
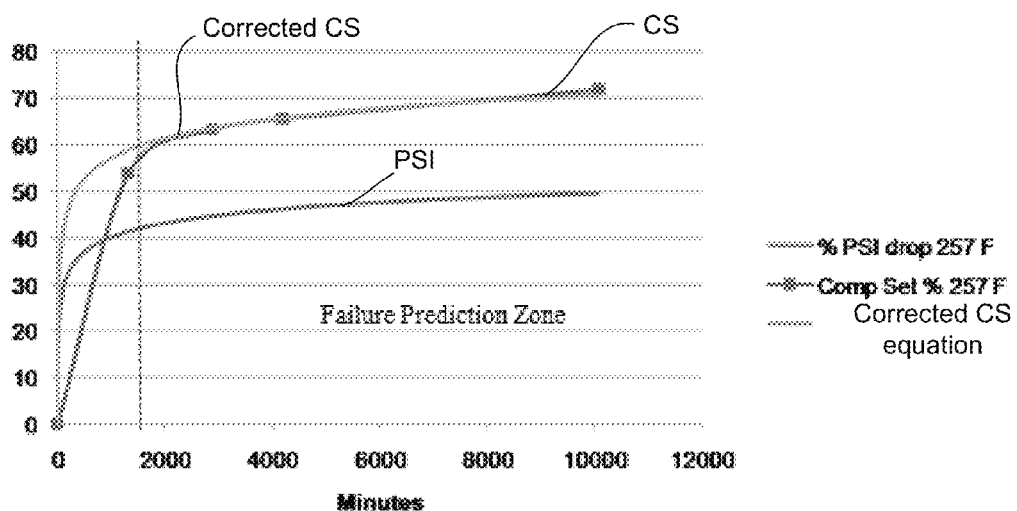

Referring to FIG. 12, pressure drop (in %) and compression set (in %) versus time for tests performed at 257° F. and a corrected pressure drop equation, which uses the $T_{CF}$ set forth above, is illustrated. As can be seen from FIG. 12, a dashed line is illustrated a time equal to approximately 1800 minutes. Data occurring after 1800 minutes is substantially linear. In addition, the corrected compression set equation closely follows the actual test data associated with the measured compression set.

Figure 13A:
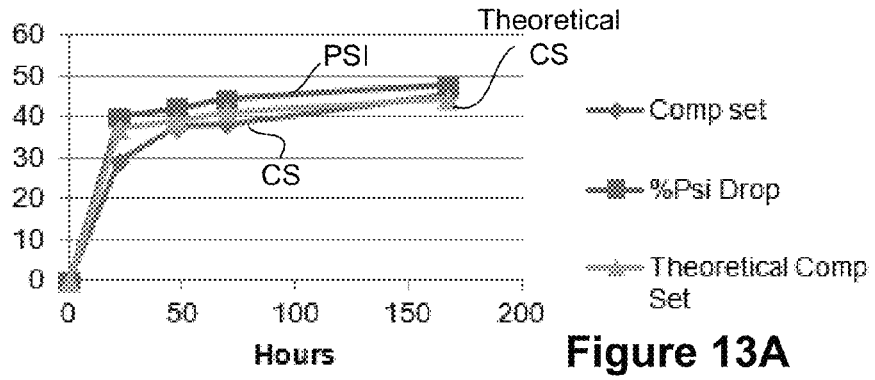
Figure 13B:
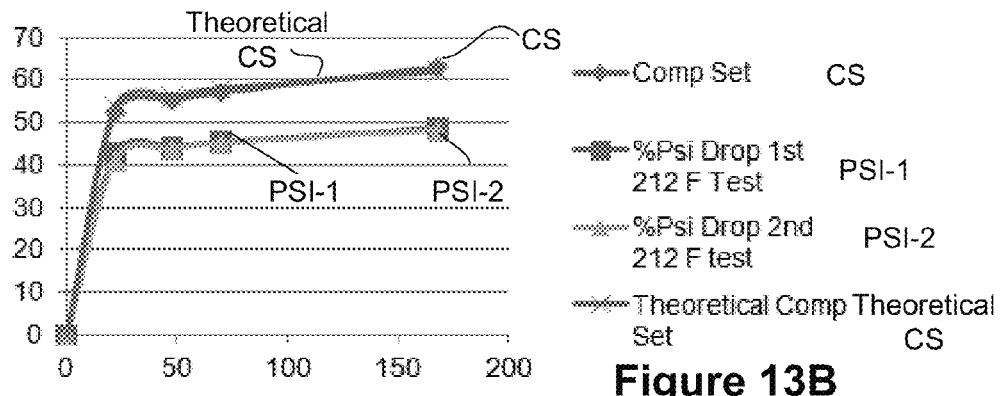
Figure 13C:
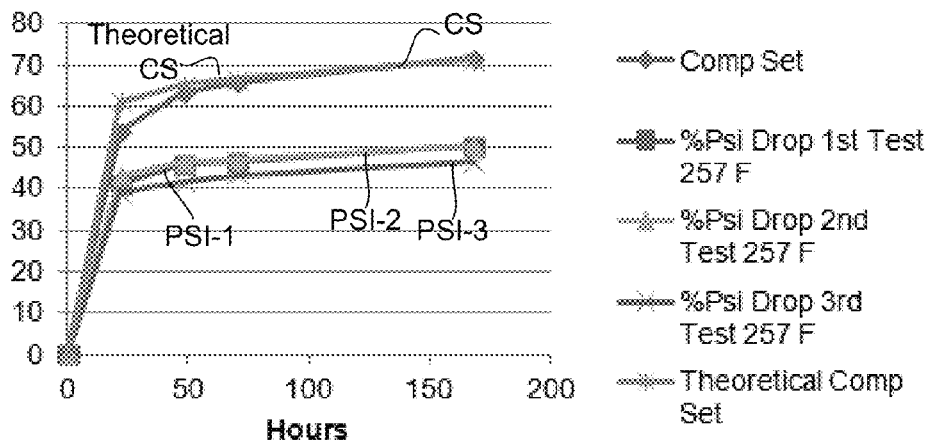

FIGS. 13A-13C illustrates theoretical results plotted with actual test data at various temperatures. For example, FIG. 13A plots compression set data versus time and pressure drop data versus time, for testing completed at 157° F. In addition, FIG. 13A also plots theoretical compression set data, based on the calculation of the Temperature Correction Factor set forth above. As can be seen from FIG. 13A, there is a direct correlation between pressure drop and compression set. The Temperature Correction Factor makes use of this relationship.

Referring to FIG. 13B, test data from two tests are illustrated (Test-1 and Test-2) and plotted as a percent of pressure drop over time for testing performed at 212° F. In addition, compression set information is also plotted as a percentage of compression set over time. Like FIG. 13A above, FIG. 13B also plots theoretical compression set data, based on the calculation of the Temperature Correction Factor for the two tests identified by Test-1 and Test-2.

Referring to FIG. 13C, test data from three tests are illustrated (Test-1, Test-2 and Test 3) and plotted as a percent of pressure drop over time for testing performed at 257° F. In addition, compression set data is also plotted as a percentage of compression set over time. Like FIGS. 13A and 13B above, FIG. 13C also plots theoretical compression set data, based on the calculation of the Temperature Correction Factor for the three tests identified by Test-1, Test-2 and Test-3.

Based on this information, a maximum compression set prediction error was determined for each temperature, as illustrated in Table 1:

| Temperature (° F.) | Max. Compression Set Prediction Error (>22 hrs) |
|---|---|
| 157 | 3.5% |
| 212 | 1.7% |
| 257 | 3.5% |

From the data presented above, it is possible to determine an amount of compression set applied to the fluid seal member by measuring an amount of force in which the fluid seal member is subjected over a period of time for wide range of application temperatures with a small error. Since the amount of compression set may be used to determine the health of the fluid seal member, the above system and method provide an indirect way of measuring health of the fluid seal member by monitoring compression applied to the fluid seal member overtime. For example, the amount of compression set above a prescribed threshold may be used to determine that the fluid seal member is in need of replacement. Such threshold may vary based on the application and the environment in which the fluid seal member is used, for example.

Figure 14:
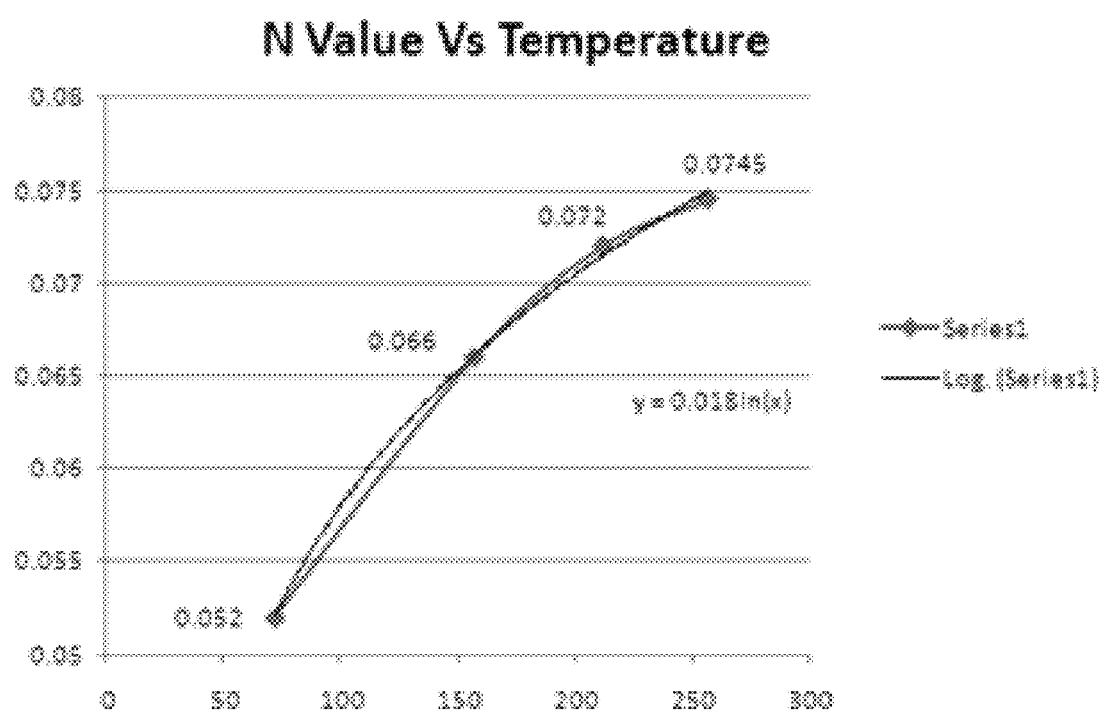
FIG. 14 is a graphical illustration of N value versus temperature in accordance with aspects of the invention.

Another aspect of the invention relates to development of a pressure prediction equation in order to provide a more comprehensive idea of fluid seal member behavior and ultimately fluid seal health at various temperatures. FIG. 14 graphically illustrates a pressure prediction exponent (n). Given the four points identified in FIG. 14, an equation $y = 0.018 \times \ln(T_F)$ is derived. Again multiple tests of various temperatures yielded similar results at the various temperatures. The following equation results:

$$PSI_t = PSI_0(t_{min})^{(-n)}$$

$PSI_0$ = Original Pressure
t = time (min)
n = pressure prediction exponent

From the above information, analytical tools may be developed to extrapolate and interpolate data in order to provide a more comprehensive understanding of fluid seal behavior and ultimately seal health at various temperatures.

Figure 15:
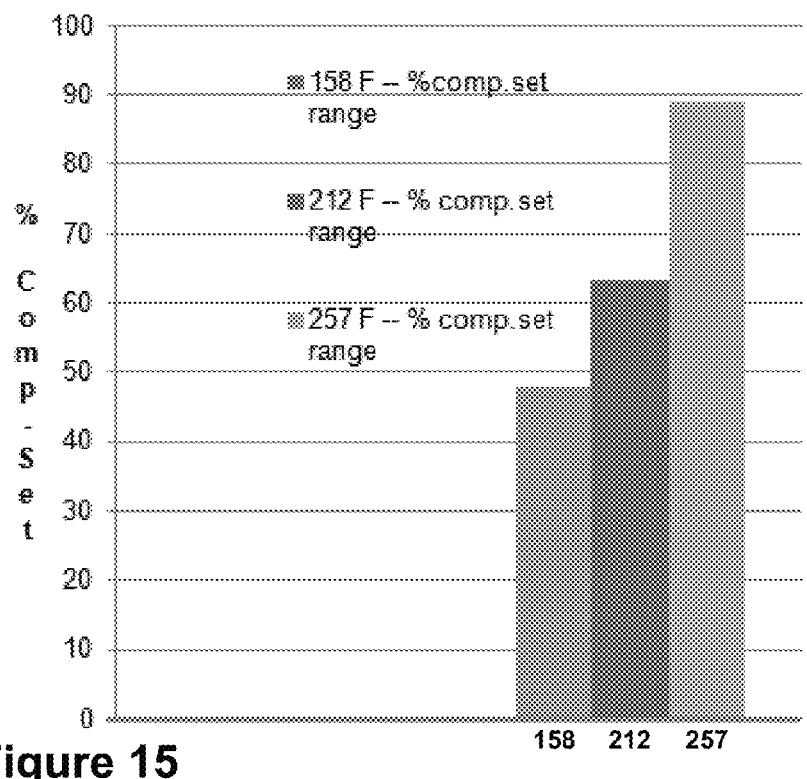
FIG. 15 is a graphical illustration of compression set range versus temperature in accordance with aspects of the invention.
Figure 16:
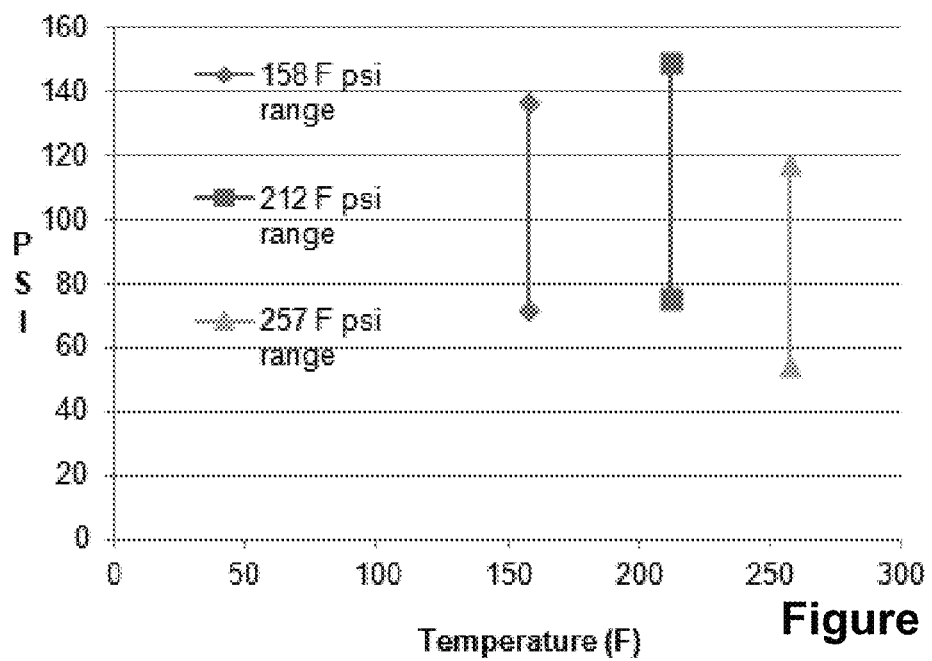
FIG. 16 is a graphical illustration of pressure range versus temperature in accordance with aspects of the invention.

FIG. 15 is a graphical illustration of the range of compression set (%) versus temperature. As illustrated by FIG. 15, the range of compression set increases based on temperature. For example increased temperature yields increase compression set, at least for the fluid seal used for these tests. FIG. 16 is a graphical illustration of the range of pressure (PSI) versus temperature (F).

Figure 17A:
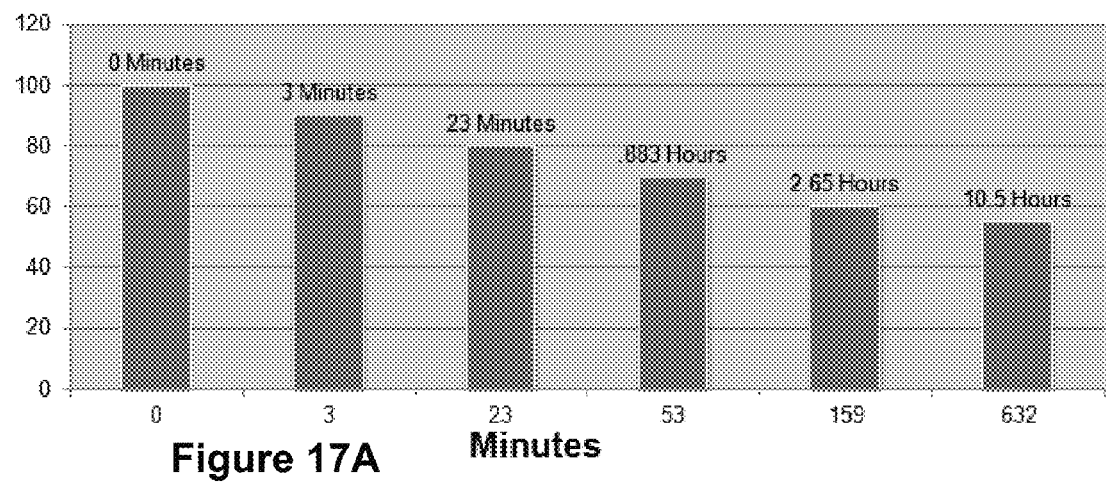
FIGS. 17A-17C are exemplary charts illustrating pressure drop over time for a plurality of temperatures.
Figure 17B:
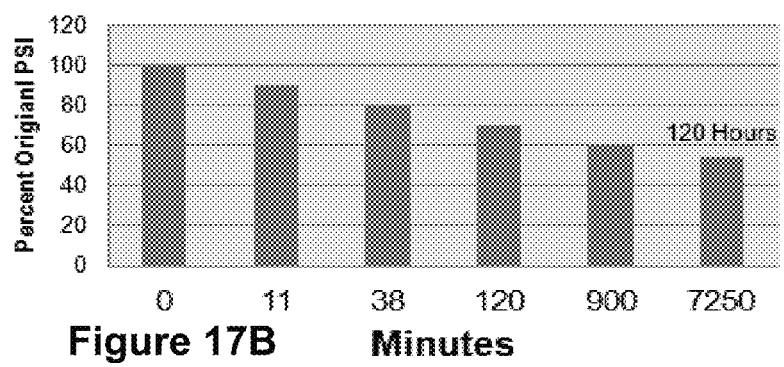
Figure 17C:
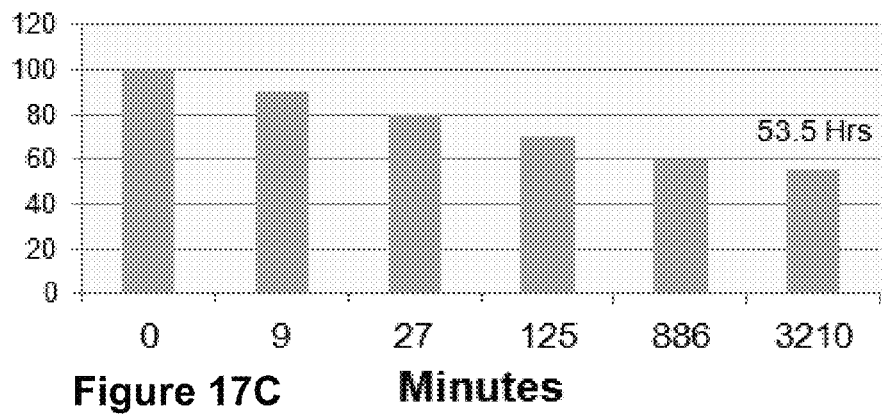

FIGS. 17A-17C illustrate pressure (PSI) drops as a function of time based on the original pressure applied to the fluid seal member for three different temperatures (e.g., 257° F. in FIG. 13A; 158° F. in FIG. 13B; and 212° F. in FIG. 13C). For example, in FIG. 17A, at time=0, 100% of the pressure is applied to the transducer through the fluid seal member. At time=3 minutes, about 90% of the original pressure is applied to the transducer through the seal. At time=23 minutes, about 80% of the original pressure is applied to the transducer through the seal. At time=53 minutes, about 70% of the original pressure is applied to the transducer through the seal. At time=159 minutes, about 60% of the original pressure is applied to the transducer through the seal. At time=632 minutes, about 55% of the original pressure is applied to the transducer through the seal.

In FIG. 17B, which corresponds to temperature of 150° F., at time=0, 100% of the pressure is applied to the transducer through the fluid seal member. At time=11 minutes, about 90% of the original pressure is applied to the transducer through the seal. At time=38 minutes, about 80% of the original pressure is applied to the transducer through the seal. At time=120 minutes, about 70% of the original pressure is applied to the transducer through the seal. At time=900 minutes, about 60% of the original pressure is applied to the transducer through the seal. At time=7,250 minutes, about 55% of the original pressure is applied to the transducer through the seal.

In FIG. 17C, which corresponds to temperature of 212° F., at time=0, 100% of the pressure is applied to the transducer through the fluid seal member. At time=9 minutes, about 90% of the original pressure is applied to the transducer through the seal. At time=38 minutes, about 80% of the original pressure is applied to the transducer through the seal. At time=2 hours, about 70% of the original pressure is applied to the transducer through the seal. At time=15 hours, about 60% of the original pressure is applied to the transducer through the seal. At time=27 minutes, about 80% of the original pressure is applied to the transducer through the seal. At time=125 minutes, about 70% of the original pressure is applied to the transducer through the seal. At time=886 minutes, about 60% of the original pressure is applied to the transducer through the seal. At time=3210 minutes, about 55% of the original pressure is applied to the transducer through the seal.

In summary, force and/or pressure detected by the transducer may be output through a RF transponder to a RF reader that is within an operable. The processor is operable to determine health of the fluid seal member based on the received output signal of the transducer, wherein the processor correlates the received output signal to a compression set and determines health of the fluid seal member by the amount of compression set imparted in the fluid seal member.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A system for determining health of a fluid seal member, the system comprising:
   a fluid seal member;
   a transducer in force transmitting contact with the fluid seal member, wherein the transducer is operable generate an output signal based on an amount of force and/or pressure applied to the transducer;
   a radio frequency (RF) transponder operably coupled to the transducer, wherein the RF transponder is configured to store the output signal of the transducer;
   a reader within an operable distance from the RF transponder, wherein the reader is selectively controlled to transmit electromagnetic energy to the RF transponder and receive the output signal of the transducer stored in the RF transponder through a radio frequency communication link; and
   a processor coupled to the reader, wherein the processor is operable to determine health of the fluid seal member based on the received output signal of the transducer, wherein the processor correlates the received output signal to a compression set and determines health of the fluid seal member by the amount of compression set imparted in the fluid seal member.

2. The system of claim 1, wherein the fluid seal member is formed of an elastomeric polymeric material.

3. The system of claim 1, wherein the elastomeric polymeric material is at least one selected from a group consisting of a natural rubber and a synthetic rubber.

4. The system of claim 1, wherein the transducer is a pressure transducer.

5. The system of claim 1, wherein the transducer is in direct contact with the fluid seal member.

6. The system of claim 1, wherein the RF transponder is a radio frequency identification (RFID) transponder.

7. The system of claim 6, wherein the RFID transponder is a passive tag.

8. The system of claim 6, wherein the RFID transponder is an active tag.

9. The system of claim 1, wherein the received output signal is a bit value.

10. The system of claim 9, wherein the processor is configured to convert the bit value into a pressure value and/or a force value.

11. The system of claim 10, further including a storage element coupled to the processor, wherein the storage element is operable to store bit values and/or pressure values for a plurality of time points.

12. The system of claim 11, wherein the processor is configured to compare the bit values and/or the pressure values for a prescribed number of time points with reference data stored in the storage element to determine the health of the fluid seal member.

13. The system of claim 12, wherein the reference data includes compression set information that is correlated to a plurality of temperatures.

14. A method for determining health of a fluid seal member, the method comprising:
    measuring force and/or pressure transmitted to the fluid seal member by a transducer in force transmitting contact with the fluid seal member and outputting an output signal corresponding to the measured force and/or pressure;
    storing a representation of the output signal in a radio frequency (RF) transponder coupled to the transducer;
    reading the representation of the output signal stored in the RF transponder by a reader, wherein the reader is selectively controlled to transmit electromagnetic energy to the RFID transponder and receive the output signal of the transducer through a radio frequency communication link; and
    processing the received output signal by a processor, wherein the processing includes determining health of the fluid seal member based on the received output signal of the transducer by correlating the received output signal to a compression set and determine health of the fluid seal member by the amount of compression set imparted in the fluid seal member.

15. The method of claim 14, wherein the transducer is in direct contact with the fluid seal member.

16. The method of claim 14, wherein the transducer is a radio frequency identification (RFID) transponder.

17. The method of claim 16, wherein the RFID transponder is a passive tag.

18. The method of claim 16, wherein the RFID transponder is an active tag.

19. The method of claim 14, wherein the received output signal is a bit value that corresponds to the force and/or pressure transmitted to the fluid seal member.

20. The method of claim 19, wherein the processor is configured to convert the bit value into a force and/or a pressure value.

21. The method of claim 20, further including causing the reader to periodically poll the RFID transducer to receive the output signal stored in the transponder and to store the received signals in a storage element coupled to the reader.

22. The method of claim 21, wherein the step of processing the received signal to determine the health of the fluid seal member includes comparing the received signals with reference data stored in the storage element to determine the health of the fluid seal member.

\* \* \* \* \*